United States Patent [19]

Kaiser et al.

[11] 4,190,591

[45] Feb. 26, 1980

[54] ODORANT AND FLAVORANT

[75] Inventors: Roman Kaiser, Uster; Peter Naegeli, Wettingen, both of Switzerland

[73] Assignee: Givaudan Corporation, Clifton, N.J.

[21] Appl. No.: 868,632

[22] Filed: Jan. 11, 1978

[30] Foreign Application Priority Data

Jan. 21, 1977 [AT] Austria .................................. 364/77
Jul. 27, 1977 [CH] Switzerland ........................ 9281/77

[51] Int. Cl.$^2$ .......................................... C07D 307/94
[52] U.S. Cl. .................................. 260/347.8; 426/536
[58] Field of Search ...................................... 260/347.8

[56] References Cited

U.S. PATENT DOCUMENTS 3,637,403   1/1972   Heckman ...................... 260/347.8 X
3,734,932   5/1973   Sakato et al. ...................... 260/347.8
4,120,830   10/1978  Renold et al. ................ 260/347.8 X

FOREIGN PATENT DOCUMENTS 1131170 10/1968 United Kingdom .

OTHER PUBLICATIONS

Demole et al., Helvetica Chimica Acta, vol. 55 (1972), pp. 1866–1882.

*Primary Examiner*—Richard Raymond
*Attorney, Agent, or Firm*—Thomas Cifelli, Jr.; Robert F. Tavares

[57] ABSTRACT

The preparation and use as odorant and/or flavorant of 2,6,10,10-tetramethyl-1-oxa-spiro-[4,5]-decan-7-one (I).

1 Claim, No Drawings

ODORANT AND FLAVORANT

FIELD OF THE INVENTION

This invention relates to the field of odorants and flavorants.

SUMMARY OF THE INVENTION

The present invention relates to a novel odorant and/or flavoring substance. More particularly, the invention is concerned with the aforementioned compound, 2,6,10,10-tetramethyl-1-oxa-spiro-[4,5]-decan-7-one, of the formula:

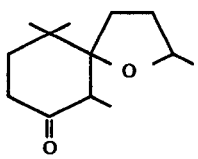

I a process for the manufacture thereof and odorant and/or flavoring compositions containing same. The invention is also concerned with a method of imparting an odor and/or flavor to materials using said compound of formula I or said compositions.

Formula I hereinbefore is intended to collectively embrace (8) stereoisomers, namely the 4 diastereomers or 4 enantiomer pairs.

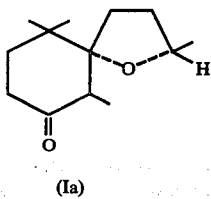

(Ia)

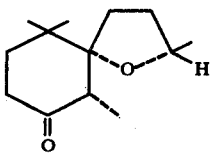

(Ib)

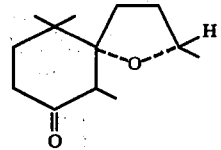

(Ic)

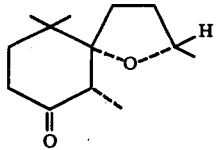

(Id)

According to the process provided by the present invention, the compound of formula I hereinbefore is manufactured by (a) cyclising 3-(3-hydroxybutyl)-2,4,4-trimethylcyclohex-2-enone, or (b) isomerising 6,7-epoxy-2,6,10,10-tetramethyl-1-oxa-spiro[4,5]-decane, or (c) oxidising 2,6,10,10-tetramethyl-1-oxa-spiro[4,5]-decan-7-ol or a compound of the general formula

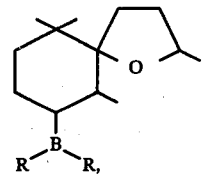

(V)

wherein R represents a hydrogen atom or an alkyl, cycloalkyl or 2,6,10,10-tetramethyl-1-oxa-spiro[4,5]-7-decyl group, or (d) reducing 6-methylene-2,10,10-trimethyl-1-oxa-spiro[4,5]-decan-7-one.

The term "alkyl" used herein means, in particular, a $C_{1-6}$-alkyl group such as the methyl, ethyl, propyl and like groups. Suitable cycloalkyl groups are, in particular, the cyclopentyl and cyclohexyl groups.

Table 1 hereinafter gives a detailed synopsis of the manufacture of the compound of formula I by embodiments (a) to (d) of the present process, and also indicates convenient practical approaches to the corresponding starting materials:

Table 1

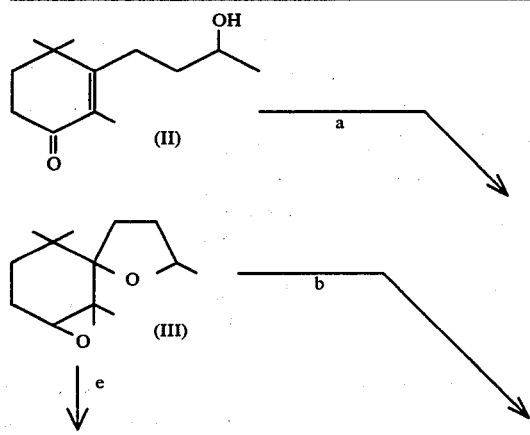

Table 1-continued

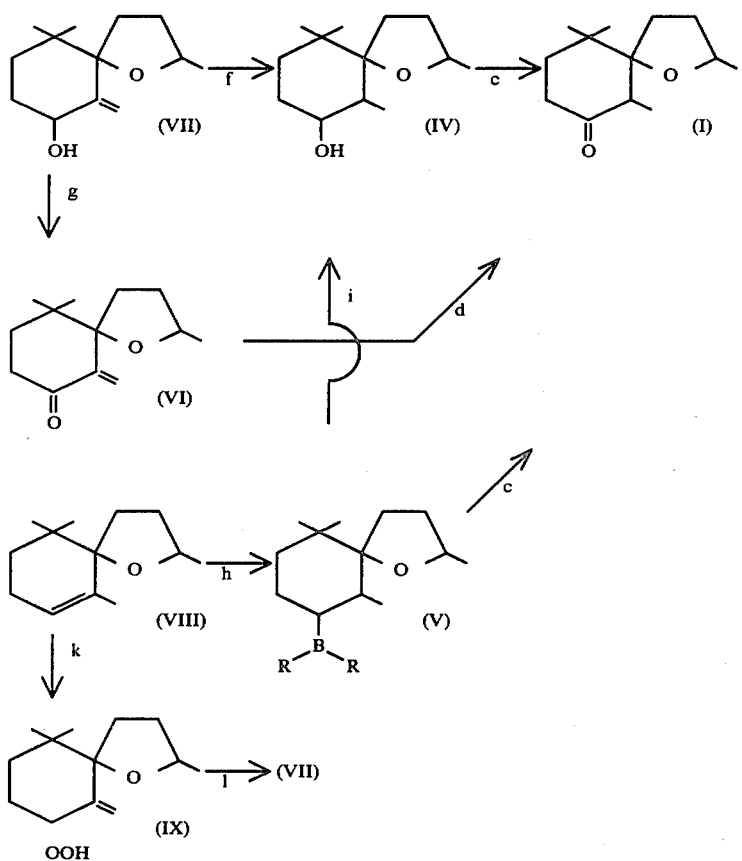

Table 2 hereinafter indicates materials and reagents as well as convenient and preferred reaction parameters for the individual embodiments of the process:

Insofar as they are not known, the starting materials required for the individual embodiments of the process (see Table 1) can be prepared as follows:

Table 2

| Process embodiment | Reaction type | Agent | preferred | Solvent | Temperature |
|---|---|---|---|---|---|
| (a) | Acid catalysis | Protonic acids Lewis acids | p-Toluenesulphonic acid perchloric acid sulphuric acid hydrochloric acid boron trifluoride hydrate ~etherate | Aliphatic or aromatic (chlorinated) hydrocarbons ether. | e.g. $-10°-100°$ |
| (b) | Acid isomerisation | Weak Lewis acids | Mg-salts, LiClO$_4$, etc | Aprotic solvents, (chlorinated) hydrocarbons, ether | e.g. $-30°-100°$ |
| (c) | Chromic acid, chromate, bichromate oxidation | Jones, Sarett*, Kiliani, Collins, Corey, Cornforth*, Brown oxidation +, etc | [see L. F. Fieser, M. Fieser, "Reagents for Organic Synthesis" John Wiley Inc. pages 142–147 (I), 54–56 (III), 95–97 (IV), 141–142 (V)] | | e.g. ca. $-20°-$ 30° C. |
| (d) | e.g. catalytic hydrogenation | Pt, Pd, Ni | [see R. L. Augustine, "Catalytic Hydrogenation" M. Dekker, New York 1965] | e.g. alcohols esters, cyclic and acyclic hydrocarbons, ether | e.g. R.T. |

*not for compound V
+ e.g. literature reference 3) p. 11

Table 3

| Step in Table 1 | Reaction type | Agent | for example | Solvent | Temperature |
|---|---|---|---|---|---|
| (e) | Isomerisation | Aluminium derivatives | diethylethoxy-aluminium, dialkylalumnium-tetramethylpiperidides, aluminium alcoholates (Al triisopropylate) | Aliphatic or aromatic hydrocarbons, alcohols (e.g. isopropanol) | 20°–150° C. |
| | | Lewis acids | $BF_3$ as the etherate or hydrate | Aliphatic or aromatic hydrocarbons (e.g. dichloromethane) | −40°–+40° C. |
| | | Protonic acids | Sulphonic acids such as p-toluenesulphonic acid, benzenesulphonic acid | Hydrocarbons (benzene, toluene) | 0°–100° C. 20°–50° C. |
| (f) | Hydrogenation | Catalysts | Pd, Pt, Rh, Ru with or without carrier (aluminium oxide, $CaCo_3$, $BaSO_4$) preferred: Pt Pd ($CaCO_3$) | Esters, hydrocarbons alcohols ethanol ethanol | 0°–50° C. (20° C.) |
| (g) | Oxidation | Activated pyrolusite, $Ag_2CO_3$ on Celite, or according to (c) for example →(see c) | Jones oxidation, chromate oxidation according to Brown 3) hexane | (Chlorinated) hydrocarbons acetone ether | 20°–100° C. −10°–30° C. −10°–35° C. |
| (h) | Hydroboration | $(R)_2BH$ $B_2H_6$ | Literature references 1) 2) | | |
| (i) | Oxidation | $H_2O_2$/NaOH | Literature references 1) 2) | | ~0°-R.T. |
| (k) see: A. Schonberg | Photo-oxidation | $O_2$, air 0°–50° C. hV (tungsten lamps UV-high pressure burner) (haematoporyphyrin, rose Bengal, etc.) | "Preparative Organic Photo- 2. Edtn. Springer Verlag 1968 | | (20° C.) |
| senstiser chemistry", | | | | | |
| (l) | Reduction | Sulphites (e.g. $Na_2SO_3$) bisulphites (e.g. $NaHSO_3$) dithionites (e.g. $Na_2S_2O_4$) etc. | Thiosulphates (e.g. $Na_2S_2O_3$) | | −10° −35° C. |

Literature
(1) H. C. Brown, Hydroboration, Benjamin Publ. N.Y. (1962) 4–38, 106-11
(2) ibid. 67–72
(3) H. C. Brown, JACS, 2951 (1961)

The compound of formula I has particular organoleptic properties, on the basis of which it is excellently suited as an odorant and/or flavouring substance.

The invention is therefore also concerned with a method of imparting an odour and/or flavour to materials, which method comprises applying to said materials or incorporating therein a flavour-imparting amount of the compound of formula I in practically pure form or in the form of mixtures (with the exception of mixtures containing the natural compound of formula I) or of an odorant and/or flavouring composition containing same.

The expression "practically pure" is used herein to mean, in particular, the compound of formula I which is free from accompanying substances which are present in addition to the compound of formula I in natural extracts. As practically pure compound I in the scope of the present invention there is to be understood, for example, the synthetically manufactured compound of formula I.

The natural mixtures containing I must, therefore, be excluded, since in the course of the foregoing work it has been found that Ia, Ib, Ic and Id are contained at a ratio of 2:1:2:1 in a quantity of 0,2–0,3% by weight in the osmanthus absolute.

The compound of formula I has a fine, woody, olfactory nuance reminiscent of dried fruits and tobacco. In addition, there are associated aspects of the odour of cedarwood oil, patchouli oil and armois oil. The compound of formula I can therefore be used, for example, for the perfuming or flavouring of products such as cosmetics (soaps, salves, powders etc), detergents or foodstuffs, luxury consumables and drinks, the compound preferably not being used alone but rather in the form of compositions which contain other odorant or flavouring substances. Such odorant or flavouring compositions containing the compound of formula I and their production in a manner known per se (the addition of the compound of formula I to known odorant or flavouring compositions or the admixture of the compound of formula I with natural or synthetic compounds or mixtures suitable as ingredients of odorant or flavouring compositions) likewise form part of the present invention.

On the basis of its very natural notes, the compound of formula I is especially suitable for the modification of known compositions such as those of the rose and chypre type, those having a generally flowery trend, and tobacco. Thus, it is very well suited, for example, for combination with green notes such as, for example, with neroli notes, as well as with flower notes such as, for example, rose, narcissus, Easterbell, broom.

It has eventually been found that the compounds I may also be used in the substitution of essential oils, such as e.g. sage oil, cedarwood oil, armois oil. In this use, there are obtained, especially, elegant round-off effects.

The concentration of the compound of formula I can vary within wide limits depending on the purpose of use; for example, between about 0.01 wt.% in the case of detergents and about 15 wt.% in the case of alcoholic solutions. In perfume bases or concentrates, the concentration can, of course, also be higher.

As a flavouring substance, the compound of formula I can be used, for example, for the production or improvement, intensification, enhancement or modification of fruit or berry aromas in foodstuffs (yoghurt, sweet goods etc), in luxury consumables (tobacco etc) and drinks (lemonades etc).

The pronounced flavour qualities of the practically pure, and especially of the synthetically manufactured, compound of formula I enables it to be used in low concentrations. A suitable range is 0.01 ppm–100 ppm, preferably 0.1 ppm–10 ppm, in the finished product (i.e. the aromatised foodstuff, luxury consumable or drink).

Table 4 hereinafter illustrates some effects which can be achieved with the compound of formula I.

Table 4

| Aroma | Amount | Effect |
|---|---|---|
| Raspberries | ppm in the finished product 0.1–30 ppm, especially 0.5–4 ppm | Emphasising the velvet-woody note of the raspberries, giving the impression of very ripe fruits |
| Apricots | ppm in the finished product 0.1–40 ppm, expecially 0.5–6 ppm | Impression of dried apricots |
| Damsons Plums Figs Grapes | ppm in the finished product 0.1–40 ppm, expecially 0.5–6 ppm | Analogous to apricots (impression of dry fruits) |

The compound of formula I can be mixed with the ingredients used for flavouring compositions or added to such flavours in the usual manner. Among the flavours contemplated according to the present invention there are to be understood flavouring compositions which can be diluted or dispersed in edible materials in a manner known per se. They can be converted according to methods known per se into the usual forms of use such as solutions, pastes or powders. The products can be spray-dried, vacuum-dried or lyophilised.

For the production of such usual forms of use there come into consideration, for example, the following carrier materials, thickening agents, flavour-improvers, spices and auxiliary ingredients:

Gum arabic, tragacanth, salts or brewers' yeast, alginates, carrageens or similar absorbants; indoles, maltol, dienals, spice oleoresins, smoke flavours; cloves, diacetal, sodium citrate; monosodium glutamate, disodium inosine-5'-monophosphate (IMP), disodium guanosine-5-phosphate (GMP); or special flavouring substances, water, ethanol, propyleneglycol, glycerine.

The following Examples illustrate the process provided by the present invention:

EXAMPLE 1

To a mixture, cooled to 0° C., of 19.4 g (0.1 mol) of 2,6,10,10-tetramethyl-1-oxa-spiro[4,5]-dec-6-ene of the formula

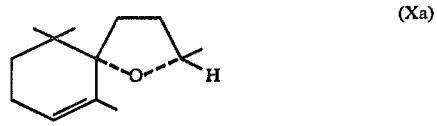

and 19.7 g of anhydrous sodium acetate in 150 ml of chloroform were added dropwise with simultaneous stirring 20.9 g (0.11 mol) of 40% peracetic acid in such a manner that the temperature was always between 5° C. and 9° C. Subsequently, the mixture was stirred for a further 2 hours at room temperature, the sodium acetate was removed by filtration, the clear solution was washed three times with water, three times with soda solution and once again with water, dried over sodium sulphate and concentrated. There were obtained 18.4 g of crude product which contained the epoxides of the formulae

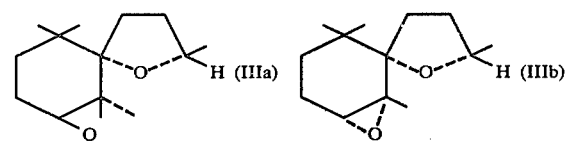

in the ratio 9:1.

15.5 g (0.074 mol) of the epoxide of formula IIIa (having a purity of greater than 98%), obtained from the previously described isomer mixture by column-chromatographical separation, were dissolved, together with 7.5 g (0.037 mol) of aluminium isopropylate, in 45 ml of isopropanol. The vessel containing this mixture was placed in an oil-bath at 170° C. and about nine-tenths of the isopropanol was distilled off via a 20 cm Vigreux column. The residual viscous mass was subsequently stirred for 2 hours at this oil-bath temperature (=a temperature of the mixture of 130°–135° C.), then cooled down to room temperature, treated with 60 ml of 30% sodium hydroxide solution, again heated to 50° C., held at this temperature for 5 minutes, further cooled down, treated with 100 ml of water and extracted with ether. The ether phase was washed three times with water, dried and concentrated. There were obtained 14.0 g of a colourless oil which, in accordance with chromatographical analysis, contained the allyl alcohol of the formula

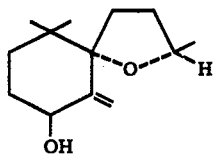
(VIIa)

in a purity of greater than 95%.

NMR: 0.85 and 0.93 (6H, 2s); 1.19 (3H, d, J=6 cps); 3.92 (1H, m); 4.47 (1H, m); 4.93 and 5.19 (2H, 2m) δ ppm, MS: m/e=210 (M+, 9), 153 (64), 141 (69), 125 (35), 111 (24), 101 (33), 95 (28), 85 (91), 70 (34), 55 (69), 43 (87), 41 (100).

13.4 g (0.064 mol) of the allyl alcohol of formula VIIa were dissolved in 50 ml of ethanol, treated with 150 mg of platinum-IV oxide and subsequently hydrogenated at normal pressure until saturated (the hydrogen consumption amounted to 1.53 liters). After filtration and concentration, there remained 13.2 g of crude product consisting, in accordance with gas-chromatographical analysis, of two components in the ratio of 2:1. Subsequent column chromatography of the crude product on a 30-fold amount of silica gel using hexane/ether (5:1) for the elution yielded 7.9 g of the alcohol of the formula

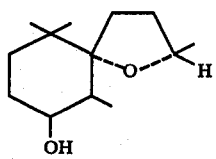
(IVa)

of melting point 74°–74.5° C.

NMR: 0.85 and 0.93 (6H, 2s); 1.00 (3H, d, J=6 cps); 1.21 (3H, d, J=6 cps); 3.90 (1H, m); 3.93 (1H, m) δ ppm MS: m/e=212 (M+, 2); 141 (100), 126 (19), 112 (21), 95 (6), 85 (28), 70 (13), 69 (13), 55 (29), 43 (30), 41 (35).

Using hexane/ether (1:1) for the elution there were obtained 3.9 g of a further purified alcohol to which can be assigned formula IVb according to spectral data. This alcohol has a melting point of 76.5°–77° C.

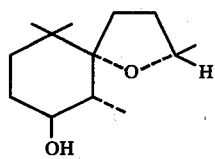
(IVb)

NMR: 0.86 and 0.96 (6H, 3s); 1.05 (3H, d, J=6 cps); 1.20 (3H, d, J=6 cps); 3.58 (1H, m); 4.20 (1H, m) δ ppm MS: 212 (M+, 4), 141 (100), 126 (13), 112 (15), 85 (21), 70 (7), 57 (14), 55 (17), 43 (17), 41 (19).

To a solution, cooled to 0° C., of 6.85 g (0.032 mol) of the alcohol of formula IVa in 30 ml of ether were allowed to drop in in the course of 5 minutes with intensive cooling and intensive stirring 30 ml of an aqueous solution, cooled to 0° C., of 9.80 g (0.032 mol) of sodium dichromate dihydrate and 8.9 g of concentrated sulphuric acid in such a manner that the temperature was between 0° C. and 3° C. Subsequently, the mixture was allowed to react for 5 minutes at 0° C. to 3° C., treated with 100 ml of ether, the ether phase was washed three times with water, three times with soda solution and again with water, dried over sodium sulphate and concentrated. There were obtained 5.1 g of a crystalline crude product which, in accordance with gas-chromatographical analysis, showed a purity of greater than 93%. It had a melting point of 89° C. after recrystallisation from pentane. According to spectral data, this product is the compound of formula Ia.

IR: 1705, 1080, 1065, 1020, 1001, 981, 965, 908 cm⁻¹

NMR: 1.00 and 1.25 (6H, 2s); 1.05 (3H, d, J~6 cps); 1.24 (3H, d, J~6 cps); 2.38 (2H, m); 3.11 (1H, q, J~6 cps); 4.10 (1H, m) δ ppm MS: m/e=210 (M+, 24), 154 (55), 139 (40), 126 (100), 112 (85), 99 (22), 83 (17), 70 (25), 56 (35), 43 (56), 41 (57).

The compound of formula Ia has a woody-cedarous odour which is accompanied by a slight amber note.

The oxidation of 3.42 g (0.016 mol) of the alcohol of formula IVb, carried out in an analogous manner, gave 2.6 g of a crystalline crude product which consisted of the spiro compound of formula Ib. The purity was greater than 93%. A sample recrystallised from pentane had a melting point of 49° C.

IR: 1710, 1089, 1070, 975, 913, 730 cm⁻¹

NMR: 0.99 and 1.20 (6H, 2s); 1.06 (3H, d, J~6 cps); 1.17 (3H, d, J~6 cps); 2.65 (1H, q, J~6 cps); 4.16 (1H, m) δ ppm MS: m/e=210 (M+, 17), 154 (47), 139 (43), 126 (80), 112 (100), 99 (20), 83 (19), 70 (33), 55 (35), 43 (41), 41 (58).

The compound of formula Ib has a woody-cedarous odour which is reminiscent of patchouli leaf oil and of dried fruits.

EXAMPLE 2

19.4 g (0.1 mol) of 2,6,10,10-tetramethyl-1-oxa-spiro[4,5]-dec-6-ene of the formula

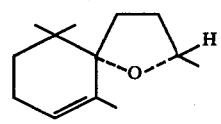
(Xb)

were epoxidised in a manner analogous to that described in Example 1. The crude product obtained (20.0 g) consisted essentially of two components in the ratio of 3:2 according to gas chromatography. After their pure isolation by column chromatography, these components were shown to be the epoxides of the formulae

 (IIIc) 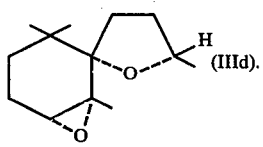 (IIId).

7.82 g (0.037 mol) of the epoxide of formula IIIc were subjected to rearrangement with aluminium isopropylate in a manner analogous to that described in Example 1. There were obtained 7.7 g of crude product which consisted to greater than 95% of the allyl alcohol of the formula

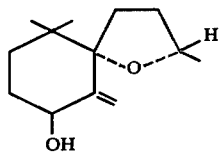

(VIIb).

An analytical sample showed, after previous bulb-tube distillation, the following spectral data:

NMR: 0.83 and 0.93 (6H, 2s); 1.20 (3H, d, J=6 cps); 4.06 (1H, m); 4.52 (1H, m); 4.95 and 5.13 (2H, 2m)

MS: m/e=210 (M+, 8), 153 (45), 141 (52), 125 (30), 111 (21), 101 (29), 95 (25), 85 (79), 70 (29), 55 (69), 43 (86), 41 (100).

The hydrogenation of 7.0 g (0.033 mol) of the allyl alcohol of formula VIIb led to two saturated alcohols in the ratio of 2:1. The subsequent column-chromatographical separation [hexane/ether (5:1)] of the crude product gave 4.0 g of the pure alcohol of the formula

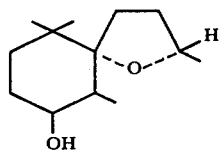

(IVc).

NMR: 0.91 and 1.00 (6H, 2s); 1.01 (3H, d, J=6 cps); 1.20 (3H, d, J=6 cps); 4.0 (2H, 2m); δ ppm MS: m/e=212 (M+, 1), 141 (100), 126 (15), 112 (28), 85 (30), 70 (15), 57 (34), 55(43), 43 (45), 41 (59).

With hexane/ether (1:1) there were eluted 2 g of a second alcohol which, after recrystallisation from ether, had a melting point of 89° C. This alcohol has the formula

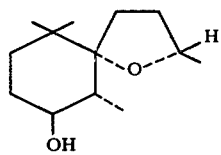

(IVd).

NMR: 0.91 (6H, 2s); 0.98 (3H, d, J=6 cps); 1.22 (3H, d, J=6 cps); 3.46 (1H, m); 4.02 (1H; m) δ ppm MS: m/e=212 (M+, 2); 141 (100), 126 (5), 112 (18), 85 (16), 70 (5), 57 (14), 55 (16), 43 (17), 41 (20).

7.1 g (0.034 mol) of the mixture of alcohols of formulae IVc and IVd, obtained by hydrogenating the allyl alcohol of VIIb, were oxidised with sodium dichromate in the manner previously described. There were obtained 6.3 g of a crystalline crude product which, in accordance with gas-chromatographical analysis, consisted of two components in the ratio of 2:1. By recrystallisation from pentane there could be obtained 2.5 g of the pure main component, the compound of formula Ic, which was eluted first in the gas-chromatogram. This compound had a melting point of 74°–74.5° C.

IR: 1702, 1081, 1060, 1050, 1020, 1001, 960, 875 cm⁻¹

NMR: 0.99 (3H, d, J∼6 cps); 1.25 (3H, d, J∼6 cps); 1.02 and 1.30 (6H, 2s); 2.35 (2H, m); 2.91 (1H, q, J∼6 cps), 4.10 (1H, m); δ ppm MS: m/e=210 (M+, 7), 154 (47), 139 (40), 126 (44), 112 (100), 99 (11), 83 (12), 70 (23), 56 (40), 43 (32), 41 (50).

The compound of formula Ic has a woody odour with slight green side-notes.

By chromatography of the remaining mother liquor on a 40-fold amount of silica gel there were obtained, by elution with hexane/ether (10:1), 1.3 g of the compound of formula Id which, after recrystallisation from pentane, had a melting point of 64° C.

IR: 1715, 1089, 1080, 1030, 1010, 975, 879 cm⁻¹

NMR: 0.97 and 1.14 (6H, 2s); 0.98 (3H, d, J∼6 cps); 1.19 (3H, d, J∼6 cps); 2.62 (1H, q, J∼6 cps); 4.00 (1H, m); δ ppm MS: m/e=210 (M+, 5), 154 (47), 139 (42), 126 (34), 112 (100), 99 (10), 83 (13), 70 (22), 56 (39), 43 (39), 41 (50).

The compound of formula Id has a woody-cedarous odour which is at the same time reminiscent of patchouli leaf oil and dried fruits.

EXAMPLE 3

70 g (0.36 mol) of 2,6,10,10-tetramethyl-1-oxa-spiro[4,5]-dec-6-ene of formulae Xa and Xb (ratio 2:1) were expoxidised according to the procedure described in Examples 1 and 2. The resulting crude product (77 g) consisted of the four isomeric epoxides of formulae IIIa, IIIb, IIIc and IIId in the ratio of ca 9:1:2:1 in accordance with gas-chromatographical analysis. This crude epoxide mixture was directly subjected to the rearrangement with aluminium isopropylate, there being obtained, after working-up and distillation, 43 g of a product (yield 57% based on the starting material) of boiling point 87°–89° C./0.15 mm Hg which contained for the most part the two allyl alcohols of formulae VIIa and VIIb. The subsequent hydrogenation using ethanol as the solvent and platinum-IV oxide as the catalyst led to a mixture of the 2,6,10,10-tetramethyl-1-oxa-spiro[4,5]-decan-7-ols of formula IV which was directly oxidised as the crude product (42 g) according to the procedure described earlier. There were obtained 37 g of crude product which consisted of the four isomers of 2,6,10,10-tetramethyl-1-oxa-spiro[4,5]-decan-7-one of formulae Ia, Ib, Ic and Id in the ratio of 4:2:2:1 in accordance with gas-chromatographical analysis.

Distillation of the crude product over a 20 cm Widmer column gave 31 g (41% based on starting material of formula Xa+Xb) as an olfactorily satisfactory product of boiling point 86°–91° C./0.06 mm Hg which possessed a woody-cedarous odour and was reminiscent of patchouli leaf oil and dried fruits.

EXAMPLE 4

A solution of 4.26 g (0.03 mol) of boron trifluoride dietherate in 4 ml of tetrahydrofuran was allowed to drop in in the course of 30 minutes to a solution of 10.5 g (0.054 mol) of the compound of formula Xa and 1.13 g (0.03 mol) of sodium borohydride in 25 ml of anhydrous tetrahydrofuran in such a manner that the temperature did not exceed 25° C. After stirring at room temperature for 16 hours, the mixture was cautiously treated with a solution of 2.16 g (0.054 mol) of sodium hydroxide in 8 ml of water and then in the course of 30 minutes with simultaneous cooling of the vessel 7.6 g (0.067 mol) of 30% hydrogen peroxide were added dropwise in such a manner that the temperature did not exceed 30° C. For completion of the reaction, the mixture was stirred for 2 hours at room temperature and then extracted with ether. The ether phase was washed with water, dried and concentrated. There were obtained 11.1 g of crude product which consisted to greater than 90% of the alcohol of formula IVb in accordance with gas-chromatographical analysis.

7.1 g of the crude alcohol of formula IVb were oxidised with sodium dichromate as described earlier. Bulb-tube distillation of the crude product (6.5 g) gave 5.1 g (67% yield based on starting material) of the crystalline compound of formula Ib (purity greater than 95%) which was contaminated with very little compound of formula Ia. A sample recrystallised from pentane had a melting point of 49° C. The same reaction sequence was likewise used on 10.5 g (0.054 mol) of 2,6,10,10-tetramethyl-1-oxa-spiro[4,5]-dec-6-ene of formula Xb (purity greater than 90%). After recrystallisation from pentane, there were finally obtained 4.3 g of the compound of formula Id (56% yield based on starting material B; purity greater than 98%). This compound had a melting point of 64° C.

EXAMPLE 5

The reaction sequence chosen for the selective preparation of the compound of formula Ib or Id (Example 4) was used on 194 g (1 mol) of the mixture of 2,6,10,10-tetramethyl-1-oxa-spiro[4,5]-dec-6-ene of formulae Xa and Xb (2:1). There were obtained 107 g of an olfactorily satisfactory mixture of the compounds of formulae Ib and Id (in the ratio of ca 2:1) of boiling point 85°-91° C./0.06 mm Hg. The yield was 51%. This isomer mixture has a woody-cedarous odour which at the same time is reminiscent of patchouli leaf oil, tobacco and distinctly of dried fruits.

EXAMPLE 6

A suspension of 5.5 g (0.145 mol) of sodium borohydride in 260 ml of ether was treated with 0.9 g of dry powdered zinc chloride, stirred for 2 hours at room temperature and then added to a solution of 77.6 g (0.4 mol) of 2,6,10,10-tetramethyl-1-oxa-spiro[4,5]-dec-6-ene of formulae Xa and Xb in 10 ml of cyclohexane. Over a period of 1 hour there was allowed to drop in a solution of 21 g (0.148 mol) of boron trifluoride dietherate in 125 ml of ether in such a manner that the temperature did not exceed 25° C. The mixture was stirred for 16 hours at room temperature, cautiously treated with 50 ml of water and there were allowed to drop in with good stirring and ice-cooling over a period of 30 minutes 450 ml of an aqueous solution of 110 g (0.369 mol) of sodium dichromate dihydrate and 80 ml of concentrated sulphuric acid in such a manner that the temperature did not exceed 30° C. After stirring for an additional 2 hours at room temperature, the mixture was extracted with ether, the ether phase was washed three times with water, three times with soda solution and again with water, dried over sodium sulphate and concentrated.

Distillation of the crude product (80.4 g) over a 20 cm Widmer column gave, in addition to 34 g of starting material, 27 g of a mixture of compounds of formulae Ib and Id in the ratio of 2:1; boiling point 84°-91° C./0.07 mm Hg; yield 32% based on starting material.

The following Examples illustrate odorant and/or flavouring compositions provided by the present invention:

EXAMPLE A

| Flowery composition | Parts by weight |
| --- | --- |
| Hydroxycitronellal | 400 |
| Linalyl acetate | 200 |

-continued

| Flowery composition | Parts by weight |
| --- | --- |
| Geraniol extra | 200 |
| Phenylethyl-phenyl acetate | 110 |
| Hexenyl salicylate | 40 |
| Cyclamen aldehyde | 20 |
| Eugenol extra | 20 |
| | 990 |

When there are added to this flowery and somewhat soap-like base 10 parts of the compound of formula I, then there appears an unexpected effect in that the composition takes on a suave, exotic, narcotic and very natural note in the direction of ylang-ylang.

EXAMPLE B

| Rose base | Parts by weight |
| --- | --- |
| Phenylethyl-phenyl acetate | 500 |
| Geraniol extra | 300 |
| α-Ionone | 60 |
| Linalool (synthetic) | 50 |
| Cinnamic alcohol (synthetic) | 40 |
| Geranyl acetate | 20 |
| Versalide (7-acetyl-1,1,4,4-tetramethyl-7-ethyl-1,2,3,4-tetralin) | 20 |
| | 990 |

When there are added to this conventional rose base 10 parts of the compound of formula I, then the resulting composition acts lighter, rounder and less sweet. From a rather harsh rose base there results a light, mild rose base. The composition acts harmoniously and much rounder.

EXAMPLE C

| Perfume base in the direction of tobacco | Parts by weight |
| --- | --- |
| α-Irisone | 200 |
| o-Tert.butyl-cyclohexyl acetate | 200 |
| Musk ketone | 100 |
| Sandalwood oil | 100 |
| α-Hexylcinnamaldehyde | 100 |
| Styrallyl acetate | 60 |
| Methyl dihydrojasmonate | 40 |
| Coumarin | 20 |
| Benzoin resinoid | 20 |
| Isobutylquinoline (10% in propyleneglycol) | 20 |
| Lavender oil | 20 |
| Vetiver oil Bourbon | 20 |
| Melilotus absolute colourless | 10 |
| Galbanum oil concentrated | 10 |
| | 920 |

The compound of formula I binds especially well with the aforementioned components. The natural tobacco effect results at first by addition of 80 parts of the compound of formula I. From a general chypre composition having a sweet-dusty character there results a very fine cedarous-amber like composition with emphasis on the tobacco-wood note.

EXAMPLE D

| Chypre base | Parts by weight |
| --- | --- |
| Bergamotte oil | 200 |
| α-Hexylcinnamaldehyde | 200 |
| Linalool extra | 200 |

-continued

| Chypre base | Parts by weight |
|---|---|
| Phenylethyl alcohol | 100 |
| Methyl dihydrojasmonate | 60 |
| Sandalwood oil | 60 |
| Oak moss absolute decolorised | 40 |
| Vetiver oil Bourbon | 20 |
| Styrallyl acetate | 20 |
| | 900 |

When there are added to this rather cologne-like chypre composition 100 parts of the compound of formula I, then there results a very pleasant soft and warm wood-chypre composition. The somewhat sharp hesperide note is suppressed; in its place there appears a rich sandal-vetiver note.

EXAMPLE E

| Fruity base | Parts by weight |
|---|---|
| Propyleneglycol | 240 |
| Hydroxycitronellal | 200 |
| Dimethylbenzylcarbinyl butyrate | 200 |
| Bergamotte oil | 100 |
| Methyl dihydrojasmonate | 100 |
| Fructone (2-methyl-1,3-dioxolan-2-ethyl acetate) | 100 |
| Maltylisobutyrate | 20 |
| β-Methyl-β-phenylglycidic acid ethyl ester (10% in propyleneglycol) | 20 |
| | 980 |

When there are added to this fresh fruit base 20 parts of the compound of formula I, then this is altered in a distinct manner in the direction of dried fruit (fig). The resulting composition acts markedly powerful and complete.

EXAMPLE F

| Green base | Parts by weight |
|---|---|
| Linalyl acetate (synthetic) | 300 |
| α-Hexylcinnamaldehyde | 240 |
| Benzyl salicylate | 200 |
| Methyl dihydrojasmonate | 100 |
| Basilicum oil | 60 |
| Linalyl anthranilate | 40 |
| Cyclal (2,4-dimethyl-3-cyclohexen-1-carboxaldehyde) (10% in propyleneglycol) | 20 |
| p-Menthane-8-thiol-3-one | 10 |
| Galbanum oil | 10 |
| | 980 |

With the addition of only 20 parts of the compound of formula I to the green, herb-like base the character thereof is totally altered in the direction of a fresh spring bloom (narcissus).

EXAMPLE G

| Apricot aroma | Parts by weight A | Parts by weight B |
|---|---|---|
| γ-Valerolactone | 0.1 g | 0.1 g |
| Ethyl vanillin | 0.5 g | 0.5 g |
| Vanillin | 1.0 g | 1.0 g |
| Butyric acid geranyl ester | 2.0 g | 2.0 g |
| Propionic acid geranyl ester | 4.0 g | 4.0 g |
| Raspberry ketone | 8.0 g | 8.0 g |
| Rum ether | 12.0 g | 12.0 g |
| Orange oil 10-fold concentrated | 13.5 g | 13.5 g |
| C-14-aldehyde | 28.0 g | 28.0 g |
| Butyric acid ethyl ester | 28.5 g | 28.5 g |
| Ketone I (10% in alcohol) | | 10.0 g |
| Propylene glycol | 902.4 g | 892.4 g |
| | 1000.0 g | 1000.0 g |

Addition of the compound of formula I to the foregoing conventional apricot aroma A brings about a distinct odoriferous alteration in that there appears in the resulting composition B a woody-fruity note. Regarding taste, there is ascertainable, in particular, a fruity-woody note, the resulting aroma being strongly reminiscent of dried apricots.

EXAMPLE H

| Raspberry Aroma | Parts by weight A | Parts by weight B |
|---|---|---|
| Palmitic acid ethyl ester | 0.05 g | 0.05 g |
| Geraniol | 0.2 g | 0.2 g |
| Methylionone | 0.6 g | 0.6 g |
| Ethyl vanillin | 1.0 g | 1.0 g |
| Valeric acid amyl ester | 1.0 g | 1.0 g |
| Acetic acid benzyl ester | 2.0 g | 2.0 g |
| C-16-aldehyde | 2.5 g | 2.5 g |
| Formic acid ethyl ester | 4.0 g | 4.0 g |
| Acetic acid amyl ester | 6.0 g | 6.0 g |
| Butyric acid ethyl ester | 6.0 g | 6.0 g |
| Acetic acid isobutyl ester | 23.0 g | 23.0 g |
| Acetic acid ethyl ester | 33.5 g | 33.5 g |
| Ketone I (10% in alcohol) | | 10.0 g |
| Propyleneglycol | 920.15 g | 910.15 g |
| | 1000.0 g | 1000.0 g |

Addition of the compound of formula I to the foregoing composition A, a conventional raspberry aroma, alters the methylionate note in an odoriferously advantageous manner in that there appears in the composition B a fruity-woody note. Regarding flavour, there is ascertainable a distinct woody-fruity note which is characteristic of raspberries.

What is claimed is:
1. Synthetically manufactured 2,6,10,10-tetramethyl-1-oxa-spiro[4,5]-decan-7-one.

* * * * *